United States Patent [19]

Jung et al.

[11] Patent Number: 5,455,356

[45] Date of Patent: Oct. 3, 1995

[54] FUNGICIDAL 1-ARYL-1-[α-(TRIAZOLYL)ALKYL]-1-SILACYCLOALKANES AND THEIR PREPARATION METHODS

[75] Inventors: Il N. Jung; Bok R. Yoo, both of Seoul; Seung H. Yeon, Kyungki, all of Rep. of Korea

[73] Assignee: Korea Institute of Science and Technology, Seoul, Rep. of Korea

[21] Appl. No.: 194,380

[22] Filed: Feb. 8, 1994

[30] Foreign Application Priority Data

Feb. 18, 1993 [KR] Rep. of Korea .................. 2239/1993

[51] Int. Cl.⁶ ........................................ C07F 7/08
[52] U.S. Cl. ........................................... 548/110
[58] Field of Search ................................ 548/110

[56] References Cited

U.S. PATENT DOCUMENTS

| | | | |
|---|---|---|---|
| 4,873,011 | 10/1989 | Jung et al. | 252/75 |
| 4,965,385 | 10/1990 | Jung et al. | 556/415 |
| 5,075,477 | 12/1991 | Jung et al. | 556/435 |
| 5,087,717 | 2/1992 | Jung et al. | 556/416 |
| 5,233,069 | 8/1993 | Jung et al. | 556/435 |
| 5,235,061 | 8/1993 | Jung et al. | 548/110 |
| 5,235,083 | 8/1993 | Jung et al. | 556/435 |
| 5,302,734 | 4/1994 | Jung et al. | 556/406 |

*Primary Examiner*—Patricia L. Morris
*Attorney, Agent, or Firm*—Oblon, Spivak, McClelland, Maier & Neustadt

[57] ABSTRACT

The novel compounds of 1-aryl-1-[α-(triazolyl)alkyl]-1-silacycloalkanes of the following formula I and their preparation are provided. The compounds of the present invention are useful in controlling fungal diseases of living plants.

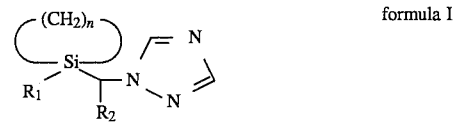

formula I wherein $R_1$ can be 4- or 2,4-substituted phenyl such as 4-fluorophenyl, 4-chlorophenyl, 4-ethoxyphenyl, 4-methoxyphenyl, 4-trifluoromethylphenyl, biphenyl, 2,4-difluorophenyl, and 2,4-dichlorophenyl and $R_2$ can be hydrogen or methyl and n is 4 or 5.

1 Claim, No Drawings

FUNGICIDAL 1-ARYL-1-[α-(TRIAZOLYL)ALKYL]-1-SILACYCLOALKANES AND THEIR PREPARATION METHODS

BACKGROUND OF THE INVENTION

1. Field of the Invention

This invention relates to 1-aryl-1-[α-triazolyl)alkyl]-1-silacycloalkanes as represented as formula I, their preparation, and their use in controlling fungal diseases of living plants.

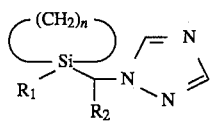

formula I wherein $R_1$ can be 4- or 2,4-substituted phenyl such as 4-fluorophenyl, 4-chlorophenyl, 4-ethoxyphenyl, 4-methoxyphenyl, 4-trifluoromethylphenyl, biphenyl, 2,4-difluorophenyl, and 2,4-dichlorophenyl and $R_2$ can be hydrogen or methyl and n is 4 or 5.

2. Description of the Prior Art

Since the late 1960's, the derivatives of azoles have been known to be useful for the control of plant diseases (M. Plempel, K. Bartmann, K. H. Bichel and Regel, *Deutsche Med. Wochen schrift*, 4, 1356–1364 (1969)). U.S. Pat. No. 3,692,798 discloses later the organosilylimidazoles of the following formula:

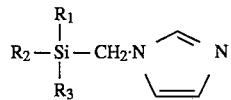

wherein $R_1$, $R_2$, and $R_3$ can be lower alkyl and phenyl. It is stated that these compounds are useful as antimicrobial agents.

German Pat. No. DE 3,000,140 discloses silyl ethers of the formula:

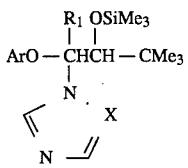

wherein Ar can be substituted phenyl, X can be CH or N, and R can be phenyl or lower alkyl. It is taught that organosilyl imidazoles or triazoles are useful as agricultural fungicides.

U.S. Pat. No. 4,510,136 discloses organosilyl group substituted at beta carbon to triazole ring represented by the following formula:

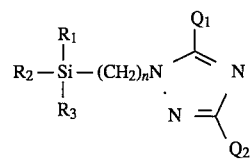

wherein $R_1$, $R_2$, and $R_3$ can be independently lower alkyl or substituted phenyl, and $Q_1$ and $Q_2$ can be independently H or $CH_3$. It is stated that the organosilyl triazoles have strong fungicidal activities and can be used to control plant fungus diseases.

The organosilyl triazoles with aromatic substituents on silicon have better fungicidal activities than the organosilyltriazoles with alkyl substituents on silicon. The triazoles with phenyl groups on silicon, having fluorine, trifluoromethyl, ethoxy, or phenyl substituent at para position show better activities than those having chloro or methyl substituent at para position.

Japanese Pat. Pub. No. 63-5092 discloses organosilyl bistriazoles of the following formula:

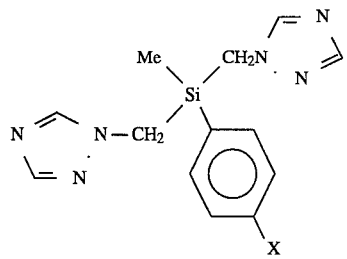

wherein X can be H, halogen, alkoxy, phenyl, substituted phenyl with halogen or lower alkyl group. It is taught that the organosilyl bistriazoles have fungicidal activities.

German Pat. DE 3,723,246 discloses organosilyl compounds having triazole and thiophene group of the formula:

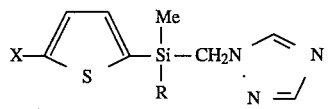

wherein X can be alkyl or halogen and R can be phenyl or substituted phenyl.

U. S. Pat. Nos. 4,530,922 and 4,729,982 also disclose the triazole compounds which are similar to the compounds disclosed in U.S. Pat. No. 4,510,136 except that alkenyl or ethynyl groups substitued on silicon instead of the methyl group. It is also stated that the compounds disclosed in the patents having thiols or thiocyanide groups substitued on the triazole ring are active.

U.S. Pat. No. 5,235,061 also discloses that (1H-1,2,4-triazolyl)disilaalkanes as represented by the following formula have fungicidal activities and can be used to control plant fungus diseases:

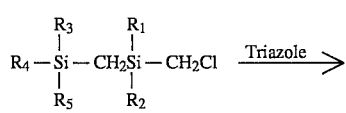

-continued

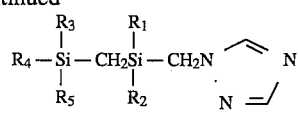

wherein $R_1$, $R_2$, $R_3$, $R_4$, and $R_5$ can be independently lower alkyl, vinyl, allyl, benzyl, or substituted phenyl such as parafluorophenyl, para-chlorophenyl, para-ethoxyphenyl and biphenyl.

SUMMARY OF THE INVENTION

We have found that 1-aryl-1-[α-(triazolyl)alkyl]-1-silacycloalkanes having 5- or 6-membered silacyclic ring as represented by formula I, have fungicidal activities and can be used to control plant Fungus diseases:

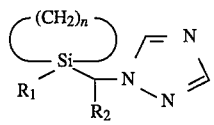

formula I wherein $R_1$ can be 4- or 2,4-substituted phenyl such as 4-fluorophenyl, 4-chlorophenyl, 4-ethoxyphenyl, 4-methoxyphenyl, -trifluoromethylphenyl, biphenyl, 2,4-difluorophenyl or 2,4-dichlorophenyl, and $R_2$ can be H or $CH_3$, and n can be 4 or 5.

DESCRIPTION OF PREFERRED EMBODIMENTS

This invention relates to novel compounds of 1-aryl-1-[α-(triazolyl)alkyl]-1-silacycloalkanes having 5- or 6-membered silacyclic ring as represented by formula I:

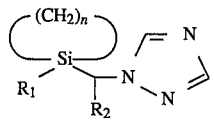

formula I wherein $R_1$ can be 4- or 2,4-substitued phenyl such as 4-fluorophenyl, 4-chlorophenyl, 4-ethoxyphenyl, 4-methoxyphenyl, -trifluoromethylphenyl, biphenyl, 2,4-difluorophenyl or 2,4-dichlorophenyl, and $R_2$ can be H or $CH_3$, and n is 4 or 5.

The present invention also relates to novel intermediate compound off 1-aryl-1-[α-(chloro)alkyl]-1-silacycloalkane as represented by formula II which is used in producing 1-aryl-1-[α-(triazolyl)alkyl]-1-silacycloalkanes:

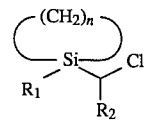

formula II wherein $R_1$ can be 4- or 2,4-substituted phenyl selected from the group consisting of 4-fluorophenyl, 4-chlorophenyl, 4-ethoxyphenyl, 4-methoxyphenyl, 4-trifluoromethylphenyl, biphenyl, 2,4-difluorophenyl, and 2,4-dichlopophenyl and $R_2$ can be hydrogen or methyl and n is 4 or 5.

The compounds of the general formula II can be prepared by reacting the compounds of chloromethyltrichloposilane and di-Grignard reagents of 1,4-dichlorobutane or 1,5-dichloropentane prepared from 1,4-dichlorobutane or 1,5-dichloropentane and magnesium metal respectively. (Chloromethyl)trichlorosilane can be prepared by chlorinating methyltrichloFosilane. In order to couple the last chlorine on silicon with aromatic group, aryl Grignard reagent or aryllithium may be used Therefore, it is not necessary to isolate the intermediate of 1-chloro-1-(α-chloroalkyl )-1-silacycloalkane, before the coupling reaction of the last chlorine on silicon with aryl Gridnard reagent or aryllithium is conducted. The Si-Cl bonds of (chloromethyl) trichlorosilane react with Grignard reagents or organolithium to form a silacyclic ring and/or to introduce organic groups, leaving the C-Cl bond unaffected.

Preferred solvents for these reactions include ethers such as diethylether, 1,2-dimethoxyethane, and tetrahydrofuran. The reaction of the (chloromethyl)-trichlorosilane with Grignard reagents or organolithium mat be conducted at any temperature of from $-20°$ C. up to $50°$ C., but below $25°$ C. is preferred.

The silacycloalkanes substituted by triazole, as represented by the formula I, can be prepared from chloromethyl containing silacycloalkanes and 1,2,4-triazole sodium salt. Lithium and potassium triazole salts may also be used. Bromomethyl or iodomethyl containing silacycloalkanes may be used instead of chloromethyl compounds. The highest yield was obtained with about 5–10% excess of the amount of triazole salt used. The reaction of triazole displacement gives better yields and proceeds faster for (iodomethyl)silanes than the corresponding (chloromethyl)silanes. (Chloromethyl)silanes may be converted to the corresponding (iodomethyl)silanes by chlorine-iodine exchange reaction using sodium iodide in acetone solution. It is often advantageous to exchange chloride for iodide before doing the triazole displacement (D. R. Baker, J. G. Fenyes, W. K. Motberg, and B. Cross Ed., "Synthesis and Chemistry of Agrochemicals: American Chemical SocLety, Washington, D.C. , 1987).

In the following examples, temperatures are given in degrees Celsius. Abbreviations for nuclear magnetic resonance (nmr) spectra are s=singlet, d=doublet, t=triplet, m= multiplet; peak positions are reported as parts per million on the basis of the internal tetramethylsilane.

EXAMPLE 1

Preparation of 1-chloromethyl-1-
(4-ethoxyphenyl )-1-silacyclopentane i) To a 250 ml, three neck, round bottomed flask equipped with a mechanical stirrer, a dropping funnel, and a reflux condenser, were added 9.65 g of magnesium species (0.400 mol) , 125 ml of THF, and 0.5 g of iodine. Through the dropping funnel was firstly added 12.7 g of 1,4-dichlorobutane (0.10 mol) and heated with heatgun to maintain at the temperature of $35°$ to $45°$ C.

ii) To a 500 ml, three neck, round bottomed flask equipped with a mechanical stirrer, a dropping funnel, and a reflux condenser, were added 18.4 g (0. 100 mol) of chloromethyltrichlorosilane and 220 ml of THF. The 1,4-diGrignard solution of 1,4-dichlorobutane prepared from procedure i) was dropwise added at $0°$ C. and stirred for 1 hr at room temperature to prepare 1-chloro-1-chloromethyl-1-silacyclopentane.

iii) To a 250 ml, three neck, round bottomed flask equipped with a mechanical stirrer, a dropping funnel and a reflux condenser, were added 2.21 g of magnesium species (0.132 mol), 100 ml of THF, and 0.5 g of iodine. Through the dropping funnel was firstly added 21.0 g of 4-ethoxybromobenzene (0.10 mol) and heated with heatgun to maintain at the temperature of 35° C. to 45° C. to prepare 4-ethoxyphenylmagnesiumbromide. After filtering excess magnesium off through a double tip needle, this Grignard solution was added to the solution prepared from the above procedure ii) and stirred for 2hrs at room temperature, quenched carefully with saturated ammonium chloride after confirming that all the starting material were reacted by gas chromatograph technique. The aqueous layer was extracted three times with hexane. The hexane solutions were combined with the organic layer and dried over magnesium sulfate. After evaporating the solvents, vacuum distillation gave 13.71 g of 1-chloromethyl-1- (4-ethoxyphenyl) -1-silacyclopentane (bp 128°–131° C./0.5 mmHg) .

EXAMPLE 2

Preparation of 1-chloromethyl-1-(4-chlorophenyl)-1-silacyclopentane i) In the same apparatus and procedures as Example 1 were reacted 8.0 g of 1,4-dichlorobutane (0.063 mol) and 6.05 g of magnesium (0.25 mol), and then followed by coupling with 12.8 g (0. 083 mol) of chloromethyltrichlorosilane to give 1-chloro-1 -chloromethyl- 1 -silacyclopentane.

ii) In the same apparatus and procedures as Example 1 was reacted 83 ml of 4-chlorophenylmagnesiumbromide solution (1.0 M in diethylether) with 1-chloro-1-chloromethyl-1-silacyclopentane prepared from the above procedure i) for 5 hrs. In the same method as Example 1 was treated the reaction product to give 5.20 g of 1-chloromethyl-1-(4-chlorophenyl)-1-silacyclopentane (b.p. 108°–110° C./0.5 mmHg).

EXAMPLE 3

Preparation of 1-chloromethyl-1-(4-fluorophenyl)-1-silacyclopentane i) In the same apparatus and procedures as Example 1 were reacted 7.9 g (0.062 mol) of 1,4-dichlorobutane and 6.0 g (0.25 mol) of magnesium species and then followed by coupling with 10.8 g (0.062 mol) of (chloromethyl)trichlorosilane in 20 ml of THF to give 1-chloro-1-chloromethyl-1-silacyclopentane.

ii) In the same apparatus and procedures as Example 1 was reacted 62 ml of 4-fluorophenylmagnesiumbromide solution (1.0 M in diethylether) with 1-chloro-1-chloromethyl-1-silacyclopentane prepared from the above procedure i) for 1 hr at 60° C. In the same method as Example 1 was treated the reaction product to give 10.34 g of 1-chloromethyl-1-(4-fluorophenyl)-1 -silacyclopentane (b.p. 98° C./0.5 mmHg).

EXAMPLE 4

Preparation of 1-chloromethyl-1-(biphenyl)-1-silacyclopentane i) In the same apparatus and procedure as Example 1 were reacted 9.5 g (0. 075 mol) of 1,4-dichlorobutane and 7.25 g (0.30 mol) of magnesium species and then followed by coupling with 13.8 g(0.075 mol) of (chloromethyl)trichlorosilane in 20 ml of FHF to give 1-chloro-1-chloromethyl-1-silacyclopentane.

ii) To a 250 ml , three neck, round bottomed flask equipped with a mechanical stirrer, a dropping funnel, and a reflux condenser, were added 2.55 g of magnesium species (0.11 mol), 90 ml of THF, and 0.5 g of iodine. Through the dropping funnel was firstly added 17.5 g (0. 075 mol) of 4-bromobiphenyl and heated with heatgun to maintain at the temperature of 35° to 45° C. to prepare biphenylmagnesiumbromide. After filtering excess magnesium off through a double tip needle, this Grignard solution was added to the solution prepared from the above procedure i) and stirred for 50 rain at room temperature. In the same method as Example 1 was treated the reaction product to give 10.53 g of 1-chloromethyl-1-(4-biphenyl)-silacyclopentane (b.p. 160°–2° C./0.5 mmHg).

EXAMPLE 5

Preparation of 1-chloromethyl-1-(2,4-difluorophenyl)1 -silacyclopentane i) In the same apparatus and procedures as Example 1 were reacted 10.0 g (0.079 mol) of 1,4-dichlorobutane and 4.9 g (0.21 mol) of magnesium species and then followed by coupling with 14.5 g (0.079 mol) of (chloromethyl)trichlorosilane in 20 ml of THF to give 1-chloro-1-chloromethyl-1-silacyclopentane.

ii) In the same apparatus and procedures as Example 4-ii) was prepared 15.3 g (0.079 mol) of 2,4-difluorophenylmagnesiumbromide solution in THF, and the followed by coupling with 1-chloro-1-chloromethyl-1-silacyclopentane prepared from the above procedure i) for 1hr at 60° C. In the same method as Example 1 was treated the reaction product to give 3.5 g of 1-chloromethyl -1-(2,4-difluorophenyl)-1-silacyclopentane (56°–7° C. /0.3 mmHg).

The compounds according to the procedure described in Example 1 through 5 are listed in Table 1.

TABLE 1

$^1$H NMR data of 1-aryl-1-(chloromethyl)-1-silacyclopentanes

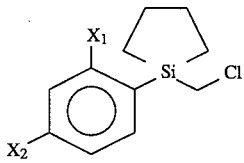

| $X_1$ | $X_2$ | $CH_2$(m, 4H) | $CH_2$(m, 4H) | $ClCH_2$(s) | aryl-H (m) | Others ($X_1$, $X_2$) |
|---|---|---|---|---|---|---|
| H | OEt | 0.86–1.07 | 1.68–1.85 | 3.06 | 6.88–7.48 | 1.44 (t, $CH_3$), 4.06 (q, $CH_2$) |
| H | OMe | 0.86–1.08 | 1.67–1.86 | 3.07 | 6.89–7.49 | 3.69 (s, $CH_3$) |

TABLE 1-continued $^1$H NMR data of 1-aryl-1-(chloromethyl)-1-silacyclopentanes

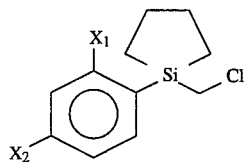

| $X_1$ | $X_2$ | $CH_2$(m, 4H) | $CH_2$(m, 4H) | $ClCH_2$(s) | aryl-H (m) | Others ($X_1$, $X_2$) |
|---|---|---|---|---|---|---|
| H | F | 0.90–1.08 | 1.64–1.81 | 3.08 | 7.35–7.54 | |
| H | Cl | 0.90–1.09 | 1.70–1.82 | 3.08 | 7.07–7.60 | |
| H | Ph | 0.99–1.08 | 1.78–1.87 | 3.17 | 7.38–7.71 | 7.38–7.71 (Ph) |
| H | $CF_3$ | 0.96–1.11 | 1.72–1.85 | 3.12 | 7.50–7.87 | |
| F | F | 0.96–1.12 | 1.68–1.81 | 3.12 | 6.75–7.50 | |
| Cl | Cl | 0.95–1.13 | 1.70–1.82 | 3.12 | 7.06–7.61 | |

EXAMPLE 6

Preparation of 1-(α-chloroethyl)-1-(4-fluorophenyl)-1-silacyclopentane i) In the same apparatus and procedures as Example 1 were reacted 3.8 g of 1,4-dichlorobutane (0.03 mol) and 1.9 g of magnesium species (0.079 mol), and then followed by coupling with 5.6. g (0.03 mol) of (α-chloroethyl)trichlorosilane to give 1-chloro-1-(α-chloroethyl)-1-silacyclopentane.

ii) In the same apparatus and procedures as Example 1 was reacted 40 ml of 4-fluorophenylmagnesiumbromide solution (2.0 M in diethylether) with 1-chloro-1-(α-chloroehtyl)-1-silacyclopentane prepared from the above procedure i) for 5hrs. In the same method as Example 1 was treated the reaction product to give 4.8 g of 1-(α-chloroethyl)-1-(4-fluorophenyl)-silacyclopentane (84°–5° C./0.3 mmHg).

The compounds according to the procedure described in Example 6 are listed in Table 2.

EXAMPLE 7

Preparation of 1-(chloromethyl)-1-(4-fluorophenyl)-1-silacyclohexane i) In the same apparatus as Example 1, was added 5.6 g of chloromethyltrichlorosilane (0.03 mol) and 50 ml of THF. Through the dropping funnel was firstly added 22 ml of 4-fluorophenylmagnesiumbromide (2.0 M in diethylether) to give chloromethyldichloro(4-fluorophenyl)silane.

ii) In the same apparatus and procedures as Example 1-i) were reacted 6.2 g of 1,5-dichloropentane (0.044 mol) and 2.8 g of magnesium species (0.11 mol), and then followed by coupling with 5.6 g (0.03 mol) of (chloromethyl)dichloro (4-fluorophenyl)silane prepared from the above procedure i) to give 3.5 g of 1-(chloromethyl)-1-(4-fluorophenyl)-1-silacyclohexane (74° C./0.2 mmHg).

The compounds according to the procedure described in Example 7 are listed in Table 3.

TABLE 2

$^1$H NMR data of 1-aryl-1-(α-chloroethyl)-1-silacyclopentanes

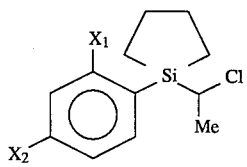

| $X_1$ | $X_2$ | $CH_2$(m, 4H) | $CH_2$(m, 4H) | $CH_3$(d, 3H) | CH(q, 1H) | aryl-H (m) | Others ($X_1$, $X_2$) |
|---|---|---|---|---|---|---|---|
| H | OEt | 0.83–1.06 | 1.25–1.79 | 1.54 | 3.65 | 6.82–7.38 | 1.37(t, $CH_3$), 3.99(q, $CH_2$) |
| H | OMe | 0.83–1.07 | 1.24–1.80 | 1.54 | 3.65 | 6.82–7.39 | 3.70 (s, $CH_3$) |
| H | F | 0.86–1.08 | 1.67–1.83 | 1.55 | 3.66 | 7.04–7.36 | |
| H | Cl | 0.87–1.09 | 1.68–1.82 | 1.55 | 3.66 | 7.20–7.59 | |
| H | Ph | 0.95–1.13 | 1.70–1.87 | 1.59 | 3.71 | 7.28–7.62 | 7.28–7.62 (Ph) |
| H | $CF_3$ | 0.89–1.14 | 1.69–1.84 | 1.56 | 3.69 | 7.19–7.59 | |
| F | F | 0.91–1.15 | 1.69–1.82 | 1.56 | 3.69 | 6.79–7.52 | |
| Cl | Cl | 0.90–1.16 | 1.70–1.83 | 1.56 | 3.68 | 7.07–7.51 | |

TABLE 3

¹H NMR data of 1-aryl-1-(chloromethyl)-1-silacyclohexanes

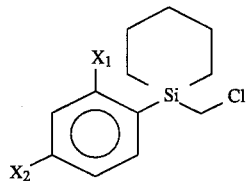

| X₁ | X₂ | CH₂(m, 4H) | CH₂(m, 2H) | CH₂(m, 4H) | ClCH₂(s) | aryl-H (m) | Others (X₁, X₂) |
|---|---|---|---|---|---|---|---|
| H | OEt | 0.92–1.11 | 1.47–1.56 | 1.69–1.85 | 3.02 | 6.85–7.54 | 1.42 (t, CH₃), 4.05 (q, CH₂) |
| H | OMe | 0.92–1.11 | 1.47–1.56 | 1.68–1.85 | 3.02 | 6.85–7.55 | 3.76 (s, CH₃) |
| H | F | 0.98–1.16 | 1.48–1.56 | 1.69–1.84 | 3.03 | 7.09–7.62 | |
| H | Cl | 0.99–1.17 | 1.48–1.57 | 1.69–1.85 | 3.03 | 7.27–7.79 | |
| H | Ph | 1.11–1.28 | 1.57–1.66 | 1.81–1.97 | 3.15 | 7.42–7.86 | 7.42–7.86 (Ph) |
| H | CF₃ | 1.01–1.19 | 1.49–1.59 | 1.69–1.85 | 3.04 | | |
| F | F | 1.00–1.19 | 1.48–1.58 | 1.69–1.85 | 3.05 | | |
| Cl | Cl | 1.01–1.19 | 1.48–1.58 | 1.69–1.85 | 3.05 | | |

EXAMPLE 8

Preparation of 1-(α-chloroethyl)-1-(4-fluorophenyl)-1-silacyclohexane i) In the same apparatus and procedures as Example 6 were reacted 10.6 g (0.051 mol) of (α-chloroethyl)trichlorosilane and 26 ml of 4-fluorophenylmagnesiumbromide (2.0 M in diethylether) to give (α-chloroethyl)dichloro(4-fluorophenyl) silane.

ii) In the same apparatus and procedures as Example 1-i) were reacted 6.5 g of 1,5-dichloropentane (0.051 mol) and 3.2 g of magnesium species (0.13 mol), and then followed by coupling with 5.6 g (0.03 mol) of (α-chloroethyl)dichloro(4-fluorophenyl)silane prepared from the above procedure i) to give 4 8 g of 1-(α-chloroethyl)-1-(4-fluorophenyl)-1-silacyclohexane (91° C./0.4 mmHg).

The compounds according to the procedure described in Example 8 are listed in Table 4.

EXAMPLE 9

Preparation of 1-iodomethyl-1-(4-ethoxyphenyl)-1-silacyclopentane

In the same apparatus as Example 1, 7.2 g (0.048 mol) of NaI was added and dissolved with 90 ml of acetone. To the flask, 8.13 g (0.032 mol) of 1-chloromethyl-1-(4-ethoxyphenyl)-1-silacyclopentane was added, and then the mixture was reacted under reflux for 5 hrs. After filtering the produced NaCl off and evaporating to remove acetone, the residue was extracted with n-hexane. The hexane solution was treated with dilute aqueous solution of Na₂S₂O₃ and dried on anhydrous MgSO₄, and filtered to remove the solvent. After confirming by NMR analysis that the halogen exchange reaction was completely carried out, the following triazole substitution reaction was directly carried out without any purification.

In the same method as above, the compounds of 1-aryl-

TABLE 4

¹H NMR data of 1-aryl-1-(β-chloroethyl)-1-silacyclohexanes

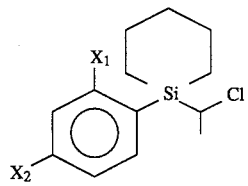

| X₁ | X₂ | CH₂(m, 4H) | CH₂(m, 4H) | CH₂(m, 2H) | CH₃(d, 3H) | ClCH(q, 1H) | aryl-H(m) | Others (X₁, X₂) |
|---|---|---|---|---|---|---|---|---|
| H | OEt | 0.90–1.06 | 1.46–1.61 | 1.79–1.90 | 1.46 | 3.56 | 6.86–7.44 | 1.36(t, CH₃), 3.97(q, CH₂) |
| H | OMe | 0.90–1.07 | 1.46–1.61 | 1.78–1.91 | 1.46 | 3.56 | 6.86–7.42 | 3.70 (s, CH₃) |
| H | F | 0.97–1.16 | 1.47–1.62 | 1.83–1.92 | 1.47 | 3.57 | 7.08–7.62 | |
| H | Cl | 0.97–1.15 | 1.48–1.63 | 1.83–1.91 | 1.47 | 3.57 | 7.21–7.41 | |
| H | Ph | 1.02–1.20 | 1.49–1.67 | 1.83–1.92 | 1.50 | 3.59 | 7.31–7.60 | 7.31–7.60 (Ph) |
| H | CF₃ | 0.98–118 | 1.48–1.65 | 1.82–1.92 | 1.49 | 3.60 | 7.29–7.60 | |
| F | F | 0.97–1.19 | 1.48–1.66 | 1.82–1.93 | 1.48 | 3.61 | 6.72–7.44 | |
| Cl | Cl | 0.97–1.17 | 1.48–1.65 | 1.81–1.93 | 1.48 | 3.60 | 6.92–7.30 | |

1-(chloromethyl) -1-silacyclopentanes,1-aryl-1-(α-chloroethyl)-1 -silacyclopentane, and 1-aryl-1-chloromethyl-1-silacyclohexanes were reacted to carry out the halogen exchange reaction.

EXAMPLE 10

Preparation of 1-(4-ethoxyphenyl)-1-(1H-1,2,4-triazole-1-yl)methyl-1-silacyclopentane To a 100 ml, round bottomed flask equipped with a condenser and a dropping funnel were added 0.29 g of NaH (0.01 mol, 80% dispersion in mineral oil) and 2 ml of DMF. After resolving 0.78 g (0.011 mol) of 1,2,4-triazole in 2 ml of dried DMF, the solution was added through the dropping funnel and the mixture was stirred for 15 min. 3.00 g (0.009 mol) of 1-iodomethyl-1-(4-ethoxyphenyl)-1-silacyclopentane as prepared in Example 9 was diluted with 3 ml of DMF to be dropwisely added to the flask, and the mixture was stirred at 45° C. for 4 and half hrs. After confirming by GC that all the reactants were participated with the reaction, the aqueous saturated $NH_4Cl$ solution was added therein, and the organic material was extracted three times 30 ml of diethylether. The extract was dried on anhydrous $MgSO_4$, and filtered to remove the solvent The residue was separated by silica gel column (eluent: ether) to obtain 2.1 g of 1-(4-ethoxyphenyl)-1-(1H-1,2,4-triazole-1-yl) methyl-1-silacyclopentane.

$^1$H-NMR($CCl_4$, δ): 0.86–0.94 (m, 4H, —$CH_2$—), 1.24–1.65 (m, 4H, —$CH_2$—), 1.38 (t, 3H, —$CH_3$), 4.00 (s, 2H, $NCH_2$—), 4.00 (q, 2H —$CH_2$—) 6.85–7.40 (m, 4H, aryl-H), 7.84 (s, 2H, Triazol-H).

EXAMPLE 11

Preparation of 1-(4-fluorophenyl)-1-(1H-1,2,4-triazole-1-yl) methyl-1-silacyclopentane In the same apparatus and procedures as Example 10 were reacted 0.21 g (0.006 mol) of NaH and 0.52 g (0.0075 mol) of 1,2,4-triazole to obtain the triazole salt. The salt was reacted with 2.0 g (0.006 mol) of 1-iodomethyl-1-(4-fluorophenyl)-1-silacyclopentane prepared in Example 9 at 15° C. for 8 hrs. The residue was separated by silica gel column (eluent: ether) to obtain 1.1 g of 1-(4-fluorophenyl)-1-(1H,1,2,4-triazole-1-yl)methyl-1-silacyclopentane.

$^1$H-NMR($CCl_4$,δ): 0.91–0.96 (m, 4H, —$CH_2$—), 1.61–1.66 (m, 4H, —$CH_2$—), 4.00 (s, 2H, $NCH_2$—), 6.99–7.49 (m, 4H, aryl-H), 7.84 (s, 1H, triazol-H), 7.85 (s, 1H, triazol-H).

EXAMPLE 12

Preparation of 1-(4-chlorophenyl)-1-(1H-1,2,4-triazole-1-yl) methyl-1-silacyclopentane In the same apparatus and procedures as Example 10 were reacted 0.20 g (0.0065 mol) of NaH and 0.49 g (0.0071 mol) of 1,2,4-triazole to obtain the triazole salt. The salt was reacted with 2.0 g (0.006 mol) of 1-iodomethyl-1-(4-chlorophenyl)-1-silacyclopentane prepared in Example 9 at 15° C. for 8 hrs. The residue was separated by silica gel column (eluent: ether) to obtain 1.2 g of 1-(4-chlorophenyl)-1-(1H-1,2,4-triazole-1-yl)methyl-1-silacyclopentane.

$^1$H-NMR($CCl_4$, δ): 0.92–0.97 (m, 4H, —$CH_2$—), 1.62–1.65 (m, 4H, —$CH_2$—), 4.01 (s, 2H, $NCH_2$—), 7.29–7.43 (m, 4H, aryl-H), 7.86 (s, 1H, triazol-H), 7.86 (s, 1H, triazol-H).

EXAMPLE 13

Preparation of 1-(4-biphenyl)-1-(1H-1, , 2 4-triazole-1-yl) methyl-1-silacyclopentane In the same apparatus and procedures as Example 10 were reacted 0.18 g (0.0058 mol) of NaH and 0.44 g (0.0064 mol) of 1,2,4-triazole to obtain the triazole salt. The salt was reacted with 2.0 g (0.0053 mol) of 1-iodomethyl-1-(4-biphenyl)-1-silacyclopentane prepared in Example 9 at 15° C. for 8 hrs. The residue was separated by silica gel column (eluent: ether) to obtain 1.2 g of 1-(4-biphenyl)-1-(1H-1,2, 4-triazole -1-yl)methyl-1-silacyclopentane.

$^1$H-NMR($CCl_4$, δ): 0.97–1.04 (m, 4H, —$CH_2$—), 1.65–1.71 (m, 4H, —$CH_2$—), 4.05 (s, 2H, $NCH_2$—), 7.35–7.60 (m, 9H, aryl-H), 7.90 (s, 1H, triazol-H), 7.91 (s, 1H, triazol-H).

The compounds according to the procedure described in Example 9 through 13 are listed in Table 5.

TABLE 5

$^1$H NMR data of 1-aryl-1-(1H-1,2,4-triazole-1-yl)methyl-1-silacyclopentanes

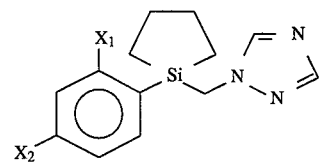

| $X_1$ | $X_2$ | $CH_2$(m, 4H) | $CH_2$(m, 4H) | $NCH_2$(s, 2H) | aryl-H(m) | triazole-H(s) | Others (X) |
|---|---|---|---|---|---|---|---|
| H | OEt | 0.86–0.94 | 1.24–1.65 | 4.00 | 6.85–7.40 | 7.84 | 1.38 (t, $CH_3$), 4.00(q, $CH_2$) |
| H | OMe | 0.86–0.95 | 1.23–1.65 | 4.00 | 6.86–7.41 | 7.84, 7.85 | 3.73 (s, $CH_3$) |
| H | F | 0.91–0.96 | 1.61–1.66 | 4.00 | 6.99–7.49 | 7.84, 7.85 | |
| H | Cl | 0.92–0.97 | 1.62–1.65 | 4.01 | 7.29–7.43 | 7.85, 7.86 | |
| H | Ph | 0.97–1.04 | 1.65–1.71 | 4.05 | 7.35–7.60 | 7.90, 7.91 | 7.35–7.60 (Ph) |
| H | $CF_3$ | 0.96–1.05 | 1.66–1.75 | 4.08 | 7.43–7.65 | 7.89, 7.90 | |
| F | F | 0.94–1.05 | 1.62–1.73 | 4.09 | 6.74–7.42 | 7.83, 7.90 | |
| Cl | Cl | 0.94–1.06 | 1.63–1.73 | 4.10 | 6.95–7.30 | 7.84, 7.91 | |

EXAMPLE 14

Preparation of
1-(4-fluorophenyl)-1-[α-(1H-1,2,4-triazole-1-yl)
ethyl]-1-silacyclopentane In the same apparatus and procedures as Example 10 were reacted 0.28 g (0.010 mol) of NaH and 0.72 g (0.011 mol) of 1,2,4-triazole to obtain the triazole salt. The salt was reacted with 2.90 g (0.0087 mol) of 1-(4-fluorophenyl)-1-(α-iodoethyl) -1-silacyclopentane prepared in Example 9 at 15° C. for 8 hrs. The residue was separated by silica gel column (eluent: ether) to obtain 1.47 g of 1-(4-fluorophenyl)-1-[α-(1H -1,2,4-triazole-1-yl)ethyl]-1-silacyclopentane.

$^1$H-NMR(CCl$_4$, δ): 0.86–1.01 (m, 4H, —CH$_2$—), 1.53–1.67 (m, 4H, —CH$_2$—), 1.56 (d, 3H, —CH$_3$), 4.18 (q, 1H, NCH—), 6.95–7.41 (m, 4H, aryl-H), 7.84 (s, 1H, triazol-H), 7.85 (s, 1H, triazol-H).

The compounds according to the procedure described in Example 14 are listed in Table 6.

TABLE 6

$^1$H NMR data of 1-aryl-1-[α-(1H-1,2,4-triazole-1-yl)ethyl]-1-silacyclopentanes

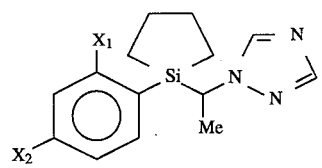

| X$_1$ | X$_2$ | CH$_2$(m, 4H) | CH$_2$(m, 4H) | CH$_3$(d, 3H) | NCH(q) | aryl-H(m) | triazole-H(s) | Others (X$_1$, X$_2$) |
|---|---|---|---|---|---|---|---|---|
| H | OEt | 0.85–0.89 | 1.23–1.66 | 1.56 | 4.17 | 6.83–7.40 | 7.83, 7.84 | 1.38(t, CH$_3$), 3.99((q, CH$_2$) |
| H | OMe | 0.86–0.89 | 1.24–1.66 | 1.56 | 4.17 | 6.84–7.41 | 7.83, 7.84 | |
| H | F | 0.86–1.01 | 1.53–1.67 | 1.54 | 4.18 | 6.95–7.41 | 7.84, 7.85 | |
| H | Cl | 0.87–1.02 | 1.52–1.68 | 1.55 | 4.18 | 7.25–7.42 | 7.85, 7.86 | |
| H | Ph | 0.91–1.05 | 1.55–1.71 | 1.57 | 4.21 | 7.30–7.59 | 7.89, 7.90 | 7.30–7.59 (Ph) |
| H | CF$_3$ | 0.92–1.05 | 1.57–1.72 | 1.57 | 4.23 | 7.31–7.60 | 7.89, 7.90 | |
| F | F | 0.91–1.04 | 1.56–1.71 | 1.58 | 4.24 | 6.71–7.38 | 7.82, 7.89 | |
| Cl | Cl | 0.91–1.05 | 1.57–1.71 | 1.58 | 4.24 | 6.89–7.29 | 7.83, 7.90 | |

EXAMPLE 15

Preparation of
1-(4-fluorophenyl)-1-(1H-1,2,4-triazole-1-yl)
methyl-1-silacyclohexane In the same apparatus and procedures as Example 10 were reacted 0.43 g (0.014 mol) of NaH and 1.10 g (0.0159 mol) of 1,2,4-triazole to obtain the triazole salt. The salt was reacted with 4.00 g (0.013 mol) of 1-iodomethyl-1-(4-fluorophenyl) -1-silacyclohexane prepared in Example 9 at 45° C. for 4 and half hrs. The residue was separated by silica gel column(eluent: ether)to obtain 1.9 g of 1-(4-fluorophenyl)-1-(1H -1,2,4-triazole-1-yl)methyl-1-silacyclohexane.

$^1$H-NMR(CCl$_4$, δ): 0.91–1.02 (m, 4H, —CH$_2$—), 1.40–1.45 (m, 2H —CH$_2$—), 1.58–1.72 (m, 4H, —CH$_2$—), 3.91 (s, 2H, NCH$_2$—), 6.97–7.41 (m, 4H, aryl-H), 7.72 (s, 1H, triazol-H), 7.81 (s, 1H, triazol-H).

The compounds according to the procedure described in Example 15 are listed in Table 7.

TABLE 7

$^1$H NMR data of 1-aryl-1-(1H-1,2,4-triazole-1-yl)methyl-1-silacyclohexanes

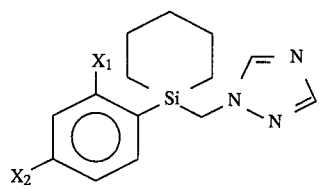

| $X_1$ | $X_2$ | $CH_2$(m, 4H) | $CH_2$(m, 2H) | $CH_2$(m, 4H) | $NCH_2$(s) | aryl-H (m) | triazole-H(s) | Others ($X_1$, $X_2$) |
|---|---|---|---|---|---|---|---|---|
| H | OEt | 0.85–1.00 | 1.40–1.44 | 1.57–1.71 | 3.90 | 6.85–7.40 | 7.71, 7.76 | 1.37(t, $CH_3$,), 3.99(q, $CH_2$) |
| H | OMe | 0.85–1.00 | 1.40–1.44 | 1.57–1.72 | 3.90 | 6.85–7.39 | 7.71, 7.77 | 3.71 (s, $CH_3$) |
| H | F | 0.91–1.02 | 1.40–1.45 | 1.58–1.72 | 3.91 | 6.97–7.41 | 7.72, 7.81 | |
| H | Cl | 0.92–1.02 | 1.40–1.46 | 1.59–1.72 | 3.92 | 7.28–7.42 | 7.73, 7.82 | |
| H | Ph | 0.96–1.14 | 1.39–1.53 | 1.71–1.83 | 4.00 | 7.33–7.66 | 7.80, 7.92 | 7.33–7.66 (Ph) |
| H | $CF_3$ | 0.95–1.09 | 1.39–1.47 | 1.58–1.73 | 3.95 | 7.34–7.59 | 7.77, 7.88 | |
| F | F | 0.94–1.08 | 1.39–1.46 | 1.58–1.73 | 3.96 | 6.72–7.41 | 7.76, 7.90 | |
| Cl | Cl | 0.94–1.09 | 1.40–1.46 | 1.57–1.73 | 3.96 | 6.94–7.29 | 7.75, 7.89 | |

EXAMPLE 16

Preparation of 1-(4-fluorophenyl)-1-[α-(1H-1,2,4-triazole-1-yl) ethyl]-1-silacyclohexane In the same apparatus and procedures as Example 15 were reacted were reacted 0.28 g (0.009 mol) of NaH and 0.7 g (0.01 mol) of 1,2,4-triazole to obtain the triazole salt. The salt was reacted with 3.4 g (0.01 mol) of 1-(α-iodoethyl)-1-(4-fluorophenyl)-1-silacyclohexane prepare in Example 9 at 45° C. for 4 and half hrs. The residue was separated by silica gel column(eluent: ether) to obtain 2.5 g of 1-(4-fluorophenyl)-1-[α-(1H -1,2,4-triazole-1-yl)ethyl]-1-silacyclohexane.

$^1$H-NMR($CCl_4$, δ): 0.79–1.87 (m, 10H, ring-$CH_2$—), 1.47 (d, 4H, —$CH_2$—), 4.10 (q, 1H, NCH—), 6.97–7.38 (m, 4H aryl-H), 7.72 (s, 1H, triazol-H), 7.83 (s, 1H, triazol-H).

The compounds according to the procedure described in Example 16 are listed in Table 8.

EXAMPLE 17

Bioactivity tests

The compounds of this invention were dissolved respectively in acetone in an amount equal to 10% of the final volume and then in purified water at the concentration of 100 ppm and 50 ppm.

Each of the solution was mixed with potato-sucrose-agar medium in 6" petri dish and one of the fungi was spotted at the center of the dish. The dish was incubated in growth room for several days. The percent disease control was derived from the radii of spore growth. The screening tests in vitro condition are well-known to those skilled in the art.

The following fungi were used for the screening.
1) Al.; Alternaria mali
2) Phy. ca.; Phytophthora capsisi
3) Phy. ha.; Physalospora baccae
4) Bo. do (Ma); Botryosphaeri
6) Py. or.; Pyricalaria oryzae

TABLE 8

$^1$H NMR data of 1-aryl-1-[α-(1H-1,2,4-triazole-1-yl)ethyl]-1-silacyclohexanes

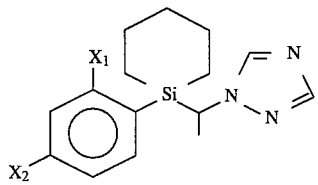

| $X_1$ | $X_2$ | ring-$CH_2$(m, 10H) | $CH_3$(d, 3H) | NCH(q, 1H) | aryl-H(m) | triazole-H(s) | Others ($X_1$, $X_2$) |
|---|---|---|---|---|---|---|---|
| H | OEt | 0.72–1.67 | 1.46 | 4.09 | 6.84–7.40 | 7.71, 7.78 | 1.35(t, $CH_3$), 3.98(q, $CH_2$) |
| H | OMe | 0.72–1.67 | 1.46 | 4.09 | 6.84–7.39 | 7.71, 7.78 | 3.71 (s, $CH_3$) |
| H | F | 0.79–1.87 | 1.47 | 4.10 | 6.97–7.38 | 7.72, 7.83 | |
| H | Cl | 0.79–1.89 | 1.47 | 4.10 | 7.29–7.60 | 7.73, 7.83 | |
| H | Ph | 0.81–1.93 | 1.51 | 4.19 | 7.33–7.58 | 7.75, 7.88 | 7.33–7.58 (Ph) |
| H | $CF_3$ | 0.89–1.98 | 1.49 | 4.16 | 7.32–7.59 | 7.76, 7.89 | |
| F | F | 0.82–1.94 | 1.48 | 4.15 | 6.72–7.41 | 7.75, 7.91 | |
| Cl | Cl | 0.82–1.93 | 1.48 | 4.15 | 6.91–7.29 | 7.74, 7.90 | |

7) Rhi. so.; Rhizoctonia solani
8) Fu. mo.; Fusarium moniliforme
9) Rhi. sp.; Rhizopus sp.

10) Bo. ci.; Botritis cinerea

TABLE 9

The percent control of 1-aryl-1-[α-(1H-triazole-1-yl)alkyl]-1-silacycloalkane derivatives to fungi

| Compounds | conc. ppm | Fungi tested and % controlled |  |  |  |  |  |  |  |  |  |
|---|---|---|---|---|---|---|---|---|---|---|---|
|  |  | AM | PC | PB | BD | GC | PO | RS | FM | RS | BC |
| 1-(4-ethoxyphenyl)-1-(1H-1,2,4-triazole-1-yl) | 200 | 100 | 100 | 84 | 89 | 100 | 100 | 100 | 79 | 77 | 74 |
| methyl-1-silacyclopentane | 50 | 100 | 40 | 80 | 82 | 100 | 100 | 72 | 68 | 66 | 70 |
| 1-(4-methoxyphenyl)-1-(1H-1,2,4-triazole-1-yl) | 200 | 100 | 100 | 85 | 79 | 100 | 100 | 100 | 80 | 75 | 77 |
| methyl-1-silacyclopentane | 50 | 100 | 41 | 79 | 75 | 100 | 100 | 74 | 70 | 64 | 72 |
| 1-(4-fluorophenyl)-1-(1H-1,2,4-triazole- | 200 | 100 | 100 | 100 | 100 | 100 | 100 | 100 | 100 | 83 | 100 |
| 1-yl)methyl-1-silacyclopentane | 50 | 100 | 80 | 100 | 100 | 100 | 100 | 95 | 10 | 75 | 100 |
| 1-(4-chlorophenyl)-1-(1H-1,2,4-triazole-1-yl) | 200 | 100 | 98 | 100 | 99 | 100 | 100 | 100 | 100 | 75 | 100 |
| methyl-1-silacyclopentane | 50 | 100 | 15 | 95 | 70 | 100 | 100 | 95 | 100 | 67 | 100 |
| 1-(4-biphenyl)-1-(1H-1,2,4-triazole-1-yl) | 200 | 94 | 100 | 94 | 72 | 100 | 100 | 93 | 100 | 72 | 30 |
| methyl-1-silacyclopentane | 50 | 68 | 68 | 92 | 72 | 100 | 100 | 89 | 47 | 69 | 15 |
| 1-(4-trifluoromethyl)-1-(1H-1,2,4-triazole- | 200 | 100 | 79 | 100 | 100 | 100 | 100 | 99 | 100 | 72 | 100 |
| 1-yl)methyl-1-silacyclopentane | 50 | 94 | 70 | 98 | 96 | 100 | 100 | 95 | 79 | 69 | 96 |
| 1-(2,4-difluorophenyl)-1-(1H-1,2,4-triazole- | 200 | 100 | 85 | 100 | 100 | 100 | 100 | 100 | 100 | 72 | 100 |
| 1-yl)methyl-1-silacyclopentane | 50 | 100 | 32 | 100 | 100 | 100 | 100 | 76 | 100 | 63 | 100 |
| 1-(2,4-dichlorophenyl)-1-(1H-1,2,4-triazole- | 200 | 100 | 79 | 100 | 100 | 100 | 100 | 100 | 100 | 70 | 100 |
| 1-yl)methyl-1-silacyclopentane | 50 | 100 | 72 | 100 | 97 | 100 | 100 | 65 | 100 | 59 | 99 |
| 1-(4-ethoxyphenyl)-1-[α-(1H-1,2,4-triazole- | 200 | 100 | 91 | 90 | 95 | 100 | 100 | 100 | 100 | 90 | 94 |
| 1-yl)ethyl]-1-silacyclopentane | 50 | 100 | 43 | 78 | 70 | 100 | 100 | 100 | 93 | 63 | 79 |
| 1-(4-methoxyphenyl)-1-[α-(1H-1,2,4-triazole- | 200 | 100 | 90 | 92 | 96 | 100 | 100 | 100 | 99 | 80 | 95 |
| 1-yl)ethyl]-1-silacyclopentane | 50 | 100 | 50 | 89 | 71 | 100 | 100 | 100 | 94 | 59 | 81 |
| 1-(4-fluorophenyl)-1-[α-(1H-1,2,4-triazole- | 200 | 100 | 100 | 100 | 100 | 100 | 100 | 100 | 100 | 75 | 100 |
| 1-yl)ethyl]-1-silacyclopentane | 50 | 100 | 45 | 100 | 100 | 100 | 100 | 100 | 94 | 59 | 100 |
| 1-(4-chlorophenyl)-1-[α-(1H-1,2,4-triazole- | 200 | 100 | 100 | 100 | 100 | 100 | 100 | 100 | 100 | 60 | 100 |
| 1-yl)ethyl]-1-silacyclopentane | 50 | 100 | 30 | 99 | 100 | 100 | 100 | 100 | 100 | 42 | 100 |
| 1-(4-biphenyl)-1-[α-(1H-1,2,4-triazole- | 200 | 100 | 100 | 100 | 100 | 100 | 100 | 100 | 100 | 90 | 100 |
| 1-yl)ethyl]-1-silacyclopentane | 50 | 100 | 80 | 100 | 100 | 100 | 100 | 100 | 97 | 86 | 100 |
| 1-(4-trifluoromethyl)-1-[α-(1H-1,2,4- | 200 | 100 | 98 | 100 | 100 | 100 | 100 | 100 | 99 | 75 | 100 |
| triazole-1-yl)ethyl]-1-silacyclopentane | 50 | 89 | 86 | 96 | 90 | 100 | 100 | 92 | 73 | 56 | 94 |
| 1-(2,4-difluorophenyl)-1-[α-(1H-1,2,4- | 200 | 100 | 94 | 100 | 100 | 100 | 100 | 100 | 100 | 87 | 100 |
| triazole-1-yl)ethyl]-1-silacyclopentane | 50 | 100 | 45 | 100 | 100 | 100 | 100 | 79 | 100 | 78 | 100 |
| 1-(2,4-dichlorophenyl)-1-[α-(1H-1,2,4-triazole- | 2W | 100 | 96 | 100 | 100 | 100 | 100 | 87 | 100 | 94 | 100 |
| 1-yl)ethyl]-1-silacyclopentane | 50 | 100 | 83 | 100 | 95 | 100 | 100 | 69 | 100 | 68 | 92 |
| 1-(4-ethoxyphenyl)-1-(1H-1,2,4-triazole-1-yl) | 200 | 100 | 87 | 95 | 100 | 100 | 100 | 100 | 99 | 85 | 94 |
| methyl-1-silacyclohexane | 50 | 100 | 65 | 87 | 79 | 100 | 100 | 94 | 73 | 54 | 74 |
| 1-(4-methoxyphenyl)-1-(1H-1,2,4-triazole-1-yl) | 200 | 100 | 93 | 93 | 100 | 100 | 100 | 100 | 92 | 79 | 89 |
| methyl-1-silacyclohexane | 50 | 100 | 49 | 82 | 85 | 100 | 100 | 96 | 81 | 65 | 69 |
| 1-(4-fluorophenyl)-1-(1H-1,2,4-triazole- | 200 | 100 | 74 | 100 | 100 | 100 | 100 | 59 | 100 | 93 | 100 |
| 1-yl)methyl-1-silacyclohexane | 50 | 100 | 47 | 100 | 100 | 100 | 96 | 55 | 100 | 75 | 100 |
| 1-(4-chlorophenyl)-1-(1H-1,2,4-triazole- | 200 | 100 | 100 | 100 | 100 | 100 | 100 | 69 | 100 | 92 | 100 |
| 1-yl)methyl-1-silacyclohexane | 50 | 100 | 90 | 100 | 100 | 100 | 100 | 57 | 100 | 50 | 100 |
| 1-(4-biphenyl)-1-(1H-1,2,4-triazole-1-yl) | 200 | 100 | 100 | 100 | 100 | 100 | 100 | 80 | 100 | 94 | 100 |
| methyl-1-silacyclohexane | 50 | 100 | 92 | 100 | 100 | 100 | 100 | 71 | 100 | 72 | 100 |
| 1-(4-trifluoromethyl)-1-(1H-1,2,4-triazole- | 200 | 100 | 99 | 97 | 100 | 100 | 100 | 80 | 98 | 76 | 100 |
| 1-yl)methyl-1-silacyclohexane | 50 | 100 | 75 | 89 | 100 | 100 | 100 | 54 | 82 | 63 | 93 |
| 1-(2,4-difluorophenyl)-1-(1H-1,2,4-triazole- | 200 | 100 | 89 | 100 | 100 | 100 | 100 | 61 | 100 | 61 | 100 |
| 1-yl)methyl-1-silacyclohexane | 50 | 100 | 67 | 100 | 100 | 100 | 100 | 41 | 100 | 53 | 100 |
| 1-(2,4-dichlorophenyl)-1-(1H-1,2,4-triazole- | 200 | 100 | 87 | 100 | 100 | 100 | 100 | 50 | 100 | 72 | 100 |
| 1-yl)methyl-1-silacyclohexane | 50 | 100 | 65 | 100 | 98 | 100 | 100 | 20 | 100 | 50 | 97 |
| 1-(4-ethoxyphenyl)-1-[α-(1H-1,2,4-triazole- | 200 | 100 | 75 | 90 | 100 | 100 | 100 | 100 | 98 | 56 | 98 |
| 1-yl)ethyl]-1-silacyclohexane | 50 | 100 | 45 | 79 | 92 | 100 | 100 | 97 | 65 | 34 | 65 |
| 1-(4-methoxoyphenyl)-1-[α-(1H-1,2,4-triazole- | 200 | 100 | 85 | 100 | 100 | 100 | 100 | 100 | 98 | 60 | 100 |
| 1-yl)ethyl]-1-silacyclohexane | 50 | 100 | 55 | 89 | 92 | 100 | 100 | 93 | 94 | 49 | 64 |
| 1-(4-fluorophenyl)-1-[α-(1H-1,2,4-triazole- | 200 | 100 | 85 | 100 | 100 | 100 | 100 | 100 | 100 | 86 | 100 |
| 1-yl)ethyl]-1-silacyclohexane | 50 | 100 | 77 | 100 | 100 | 100 | 100 | 100 | 100 | 76 | 100 |
| 1-(4-chlorophenyl)-1-[α-(1H-1,2,4-triazole- | 200 | 100 | 100 | 100 | 100 | 100 | 100 | 100 | 100 | 90 | 100 |
| 1-yl)ethyl]-1-silacyclohexane | 50 | 100 | 75 | 100 | 100 | 100 | 100 | 100 | 100 | 77 | 100 |
| 1-(4-biphenyl)-1-[α-(1H-1,2,4-triazole- | 200 | 100 | 100 | 100 | 100 | 100 | 100 | 100 | 100 | 89 | 100 |
| -1-yl)ethyl]-1-silacyclohexane | 50 | 100 | 92 | 100 | 100 | 100 | 100 | 100 | 100 | 79 | 100 |
| 1-(4-trifluoromethyl)-1-[α-(1H-1,2,4- | 200 | 100 | 78 | 100 | 100 | 100 | 100 | 100 | 99 | 56 | 99 |
| triazole-1-yl)ethyl]-1-silacyclohexane | 50 | 100 | 39 | 95 | 100 | 100 | 100 | 99 | 58 | 47 | 66 |
| 1-(2,4-difluorophenyl)-1-[α-(1H-1,2,4- | 200 | 100 | 100 | 100 | 100 | 100 | 100 | 100 | 100 | 79 | 100 |
| triazole-1-yl)ethyl]-1-silacyclohexane | 50 | 100 | 82 | 100 | 100 | 100 | 100 | 96 | 100 | 53 | 100 |
| 1-(2,4-dichlorophenyl)-1-[α-(1H-1,2,4-triazole- | 200 | 100 | 100 | 100 | 100 | 100 | 100 | 100 | 100 | 60 | 100 |
| 1-yl)ethyl]-1-silacyclohexane | 50 | 100 | 64 | 100 | 100 | 100 | 100 | 100 | 100 | 54 | 100 |

What is claimed is:

1. A 1-aryl-1-[α-(triazolyl)alkyl]-1-silacycloalkane compound represented by formula I:

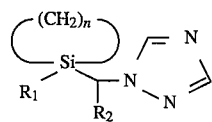
formula I
wherein $R_1$ can be 4- or 2,4-substituted phenyl from the group consisting of 4-fluorophenyl, 4-chlorophenyl, 4-ethoxyphenyl, 4-methoxyphenyl, 4-trifluoromethylphenyl, biphenyl, 2,4-difluorophenyl and 2,4-dichlorophenyl, and $R_2$ can be H or $CH_3$, and n is 4 or 5.
* * * * *